United States Patent
Mueting et al.

(10) Patent No.: US 7,659,725 B2
(45) Date of Patent: Feb. 9, 2010

(54) METHOD FOR ASSESSING THE SUITABILITY OF METERED DOSE INHALER ACTUATORS

(75) Inventors: Michael W. Mueting, Stillwater, MN (US); Stephen W. Stein, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/293,195

(22) PCT Filed: Mar. 22, 2007

(86) PCT No.: PCT/US2007/064675

§ 371 (c)(1), (2), (4) Date: Sep. 16, 2008

(87) PCT Pub. No.: WO2007/112271

PCT Pub. Date: Oct. 4, 2007

(65) Prior Publication Data

US 2009/0121722 A1    May 14, 2009

Related U.S. Application Data

(60) Provisional application No. 60/785,619, filed on Mar. 24, 2006.

(51) Int. Cl.
G01R 29/12 (2006.01)
A61M 11/00 (2006.01)

(52) U.S. Cl. .................................. 324/457; 128/200.23

(58) Field of Classification Search ................ 324/457; 128/200.14, 200.21–200.24, 203.12, 203.15, 128/204.18, 204.21, 204.22; 222/1, 402.24, 222/402.1–402.2, 160, 162, 251, 394

See application file for complete search history.

(56) References Cited

U.S. PATENT DOCUMENTS 4,321,546 A * 3/1982 Schneider, Jr. .............. 324/457

| 4,664,107 | A | 5/1987 | Wass |
|---|---|---|---|
| 4,819,834 | A | 4/1989 | Thiel |
| 5,433,498 | A | 7/1995 | Ishiwata |
| 5,772,085 | A | 6/1998 | Bryant et al. |
| 5,836,299 | A | 11/1998 | Kwon |
| 5,887,586 | A | 3/1999 | Dahlback et al. |
| 6,089,227 | A | 7/2000 | Nilsson |
| 6,454,140 | B1 | 9/2002 | Jinks |
| 6,571,793 | B1 | 6/2003 | Nilsson |
| 6,615,826 | B1 | 9/2003 | Gabrio et al. |
| 6,640,805 | B2 | 11/2003 | Castro et al. |
| 6,644,517 | B2 | 11/2003 | Thiel et al. |
| 6,650,805 | B2 | 11/2003 | Chen et al. |
| 6,868,853 | B1 | 3/2005 | Nilsson et al. |
| 6,932,082 | B2 | 8/2005 | Stein |
| 7,073,499 | B1 * | 7/2006 | Reinhold et al. ....... 128/200.18 |
| 2003/0010794 | A1 | 1/2003 | Herdtle et al. |

(Continued)

FOREIGN PATENT DOCUMENTS

WO  WO 2004/022142  3/2004
WO  WO 2004/022143  3/2004

Primary Examiner—Hoai-An D Nguyen

(57) ABSTRACT

A method of assessing the suitability of a metered dose inhaler actuator A test canister equipped with a valve and containing a pressurized propellant is provided. One or more actuators manufactured for use in a metered dose inhaler is provided and tested, wherein each actuator is tested by coupling the canister to the actuator, positioning the actuator with respect to an electrostatic measurement device and firing the canister such that electrostatic charge from an aerosol emitted by the canister is measured by the electrostatic measurement device. The measured electrostatic charge is compared to a predetermined specification range to make a determination whether the measured electrostatic charge is within or outside the predetermined specification range and accordingly whether the actuator is or is not acceptable.

17 Claims, 3 Drawing Sheets

U.S. PATENT DOCUMENTS

| | | |
|---|---|---|
| 2003/0089368 A1 | 5/2003 | Zhao |
| 2003/0121935 A1 | 7/2003 | Arsenault et al. |
| 2003/0127464 A1 | 7/2003 | Bryant et al. |
| 2003/0178022 A1 | 9/2003 | Davies et al. |
| 2005/0016527 A1* | 1/2005 | Barger et al. ........... 128/200.23 |
| 2005/0025213 A1* | 2/2005 | Parks ............................ 374/5 |

* cited by examiner

METHOD FOR ASSESSING THE SUITABILITY OF METERED DOSE INHALER ACTUATORS

CROSS REFERENCE TO RELATED APPLICATIONS

This application is a national stage filing under 35 U.S.C. 371 of PCT/US2007/064675, filed Mar. 22, 2007, which claims priority to U.S. Provisional Application No. 60/785, 619, filed Mar. 24, 2006, the disclosure of which is incorporated by reference in its/their entirety herein.

CROSS-REFERENCE TO RELATED CASES

The present invention claims priority to U.S. provisional application 60/785,619, filed Mar. 24, 2006.

FIELD

The present invention relates to methods for assessing the suitability of metered dose inhaler actuators.

BACKGROUND

Metered dose inhalers (MDIs) are commonly used to treat a number of medical conditions. Typical medicinal formulations, i.e., solutions or suspensions of drug in a propellant, are housed within a pressurized canister and emitted as an aerosol in controlled amounts by a metering valve acting in conjunction with an actuator. The actuator will generally have a mouthpiece, through which the emitted aerosol may be inhaled by a patient. It is important that the amount of drug reaching a patient with each actuation of the metering valve be a consistent amount, so as to avoid over- or under-dosing of a patient. The form in which the drug is released may also play an important role in providing consistent dosing to a patient. That is, characteristics of the aerosol plume delivered by an MDI, such as the average particle size, the particle size distribution, or the distribution of drug within the particles in the plume, may influence the ultimate effective dose that a patient receives.

SUMMARY OF THE INVENTION

In one embodiment, the present invention is a method of assessing the suitability of a metered dose inhaler actuator. A test canister equipped with a valve and containing a pressurized propellant is provided. One or more actuators manufactured for use in a metered dose inhaler is provided and tested, wherein each actuator is tested by coupling the canister to the actuator, positioning the actuator with respect to an electrostatic measurement device and firing the canister such that electrostatic charge from an aerosol emitted by the canister is measured by the electrostatic measurement device. The measured electrostatic charge is compared to a predetermined specification range to make a determination whether the measured electrostatic charge is within or outside the predetermined specification range and accordingly whether the actuator is or is not acceptable.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers may be used throughout the figures to denote like parts.

DETAILED DESCRIPTION

Figure 1:
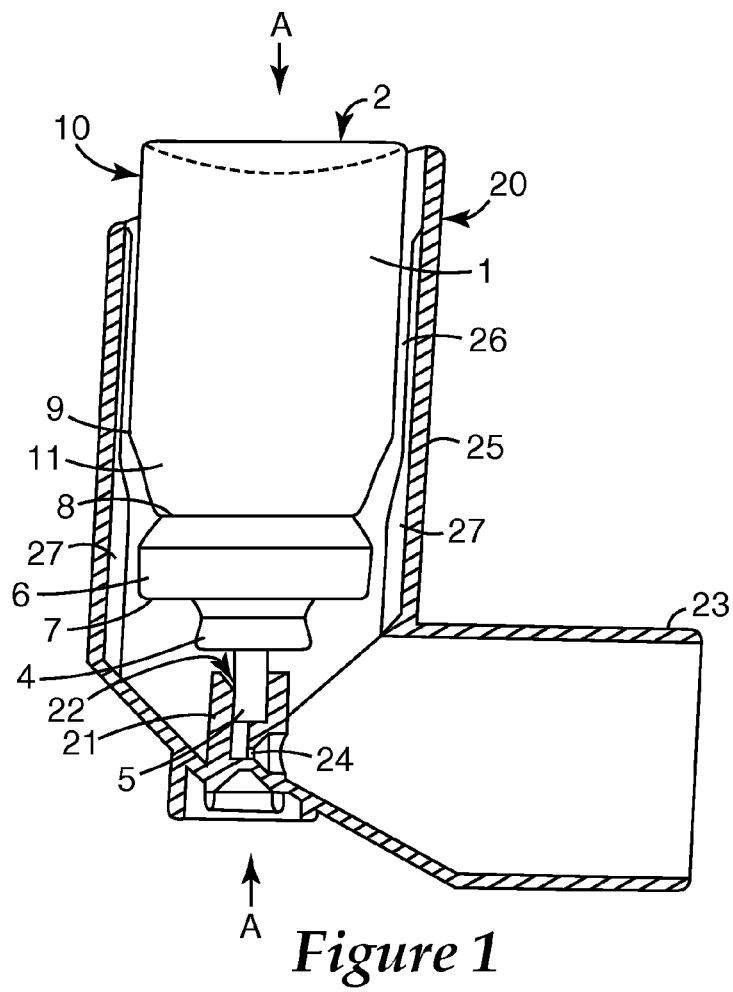
FIG. 1 is a partial cross-sectional side view of a conventional press-and-breath-type of pressurized metered dose inhaler.

An exemplary pressurized metered dose inhaler which may be used in one embodiment of the present invention is shown in FIG. 1. The inhaler comprises a test canister 10 and an actuator 20. The test canister typically comprises a substantially cylindrical container 1, in particular an aerosol container, having a closed end 2, which is typically concave in form, and an open end (not visible). The open end of the container is equipped with a dispensing means 4, in particular, a dispensing valve, more particularly a metering dose valve, having an elongate outlet member 5, in particular a valve stem, movable between closed and discharged positions. The dispensing means is normally mounted onto the container by means of a ferrule 6. The ferrule is typically fastened onto the container by crimping, however it can be suitably fastened onto the container by other means, such as welding, adhesives, snap-fit, or thread-fit. The term ferrule is understood here to mean any component or element of the dispensing canister, which is used to allow the attachment of the dispensing means to the container. The ferrule may be an integral component of the dispensing means or an integral component of the container or alternatively be a separate component, e.g. in the form of a mounting ring or cup. After fastening (e.g. crimping), the ferrule typically shows a seal-edge 7 (e.g. a folded edge) near the open end of the container and an upper edge or boundary 8 (e.g. a crimped edge) about the container. The container 1 may have a constricted portion 11 adjacent to the upper edge of the ferrule with the container then having a shoulder 9 in the vicinity of the upper edge of the ferrule. The actuator 20 typically comprises a support block 21 having a socket 22. The outlet member 5 of the test canister 10 (e.g. the dispensing end of the elongate valve stem of a metered dose dispensing valve) is received by the socket 22 and thus positioned in the support block 21. The support block 21 and orifice 24 will define an exit channel that allows pressurized formulation to pass from the outlet member 5 into the mouthpiece 23. The container 1 and the support block 21 are reciprocally movable relative to each other along an axis, marked as "A". The actuator typically includes a patient port, such as a mouthpiece 23 and the support block has an orifice 24 having open communication with the socket and the mouthpiece 23. The actuator also typically includes an elongate or generally cylindrical portion 25 extending opposite the support block defining a chamber 26 to accommodate at least a portion of the container 1 of the dispensing-canister. One or more ribs 27 positioned within the chamber of the cylindrical portion aid in locating and supporting the container in the correct position. The container 1 holds a pressurized formulation, that in one embodiment may comprise a medicinal ingredient.

It should be understood that any other type of metered dose inhaler may be suitable for use in the present invention. Examples of suitable pressurized aerosol devices useful with methods of the present invention include metered dose inhalers described in U.S. Pat. No. 4,664,107 (Wass); U.S. Pat. No. 4,819,834 (Thiel), U.S. Pat. No. 5,772,085 (Bryant et al.), U.S. Pat. No. 5,836,299 (Kwon), and U.S. Pat. No. 6,650,805 (Castro et al.), the disclosures of which are hereby incorporated by reference. Metered dose inhalers having various types of valve arrangements, such as those described in U.S. Pat. No. 5,772,085 (Bryant et al.), U.S. Pat. No. 6,454,140 (Jinks), U.S. Pat. No. 6,644,517 (Thiel et al.), and U.S. Pat. No. 6,640,805 (Castro et al.); U.S. Published Patent Applications Nos. 2003/010794 (Herdtle et al.), 2003/127464 (Bryant et al.), and 2003/121935 (Arsenault et al.) and International Publication Nos. WO 04/22143 (Greenleaf et al.) and WO 04/22142 (Hodson) are also suitable.

Any type of metered dose actuator may be suitably assessed by methods in accordance to the present invention. Examples of suitable actuators, include those described in U.S. Pat. No. 5,433,498 (Sioutas), U.S. Pat. No. 6,615,826 (Gabrio et al.), and U.S. Pat. No. 6,932,082 (Stein), and U.S. Published patent Applications Nos. 2003/178022 (Davies et al.) and 2003/089368 (Zhao). Examples of suitable actuators include those used on commonly available metered dose inhalers, such as QVAR™ (available from Ivax Co.), Proventil® HFA (available from Shering-Plough,), Ventolin® HFA, Serevent®, Flovent® HFA (available from GlaxoSmithKline), Combivent®, Atrovent® (available from BoehringerIngelheim), Xopenex HFA® (available from Sepracor, Inc.), Aerobid® (available from Forest Laboratories, Inc.), and Maxair™ (available from 3M Co.). Actuators will typically have an orifice diameter of between about 0.10 to 0.45 mm, often between about 0.15 to 0.45 mm, and sometimes between about 0.25 to 0.42 mm. In one embodiment, the orifice and support block may be formed as an integral portion of the actuator. For example, the actuator may be formed as a single molded piece incorporating all necessary functional features. The actuator will typically be formed in a polymeric molding process, such as injection molding. Suitable polymeric materials include polyethylene, polypropylene, polymethylmethacrylate, polyethylene terephthalate, polyetheretherketone, and polycarbonate. Blends or combinations of materials may also be suitable or the materials may be of a composite structure. For example, the material may comprise a base substrate and a layer coating the substrate. The base substrate material may comprise any of the aforementioned materials, or any other suitable material. The coating layer may include a fluoropolymer, silicone or fluorosilicone based material or other material or material blend with low adhesion properties, which is smooth, and/or which possesses low surface energy. In another embodiment, one or more separate components may be assembled to form the support block and define the exit channel connecting the outlet of the canister to the mouthpiece of the actuator.

Figure 2:
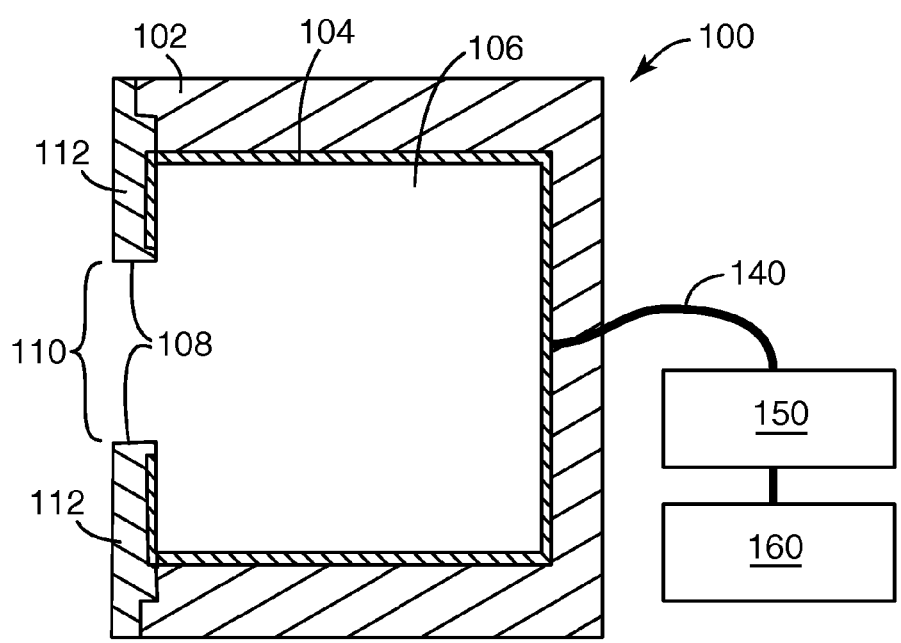
FIG. 2 is a cross-sectional side view and schematic of an electrostatic charge measurement device.

An electrostatic measurement device is shown in FIG. 2. The device 100 has an outer, non-conductive housing 102 and adaptor 112 that define an interior cavity 106. The interior cavity 106, shown in cross-section, has an inner, conductive lining 104 and may take any desired shape in three dimensions, such as a cylinder or a cube. The interior cavity 106 is completely enclosed with the exception of an opening 110 defined by sidewalls 108 in the adaptor 112. The device housing 102, adaptor 112, and lining 104 serve as the detection portion of the device and are often referred to as a Faraday cup. The adaptor 112 may be fixed to the housing 102, or may optionally be removable, for example, to facilitate cleaning of the inner, conductive lining 104. The conductive lining 104 may be slightly recessed from the sidewalls 108, so that the sidewalls 108 are non-conductive. The opening 110 is sized so as to be able to receive a metered dose inhaler actuator, such as that shown in FIG. 1. The conductive lining 104 is connected by a wire 140 to electronics 150 capable of measuring the electrostatic charge deposited on the lining 104. The electronics 150 are in turn connected to a meter 160 or other recording device where the measured electrostatic charge is displayed or output.

Figure 3:
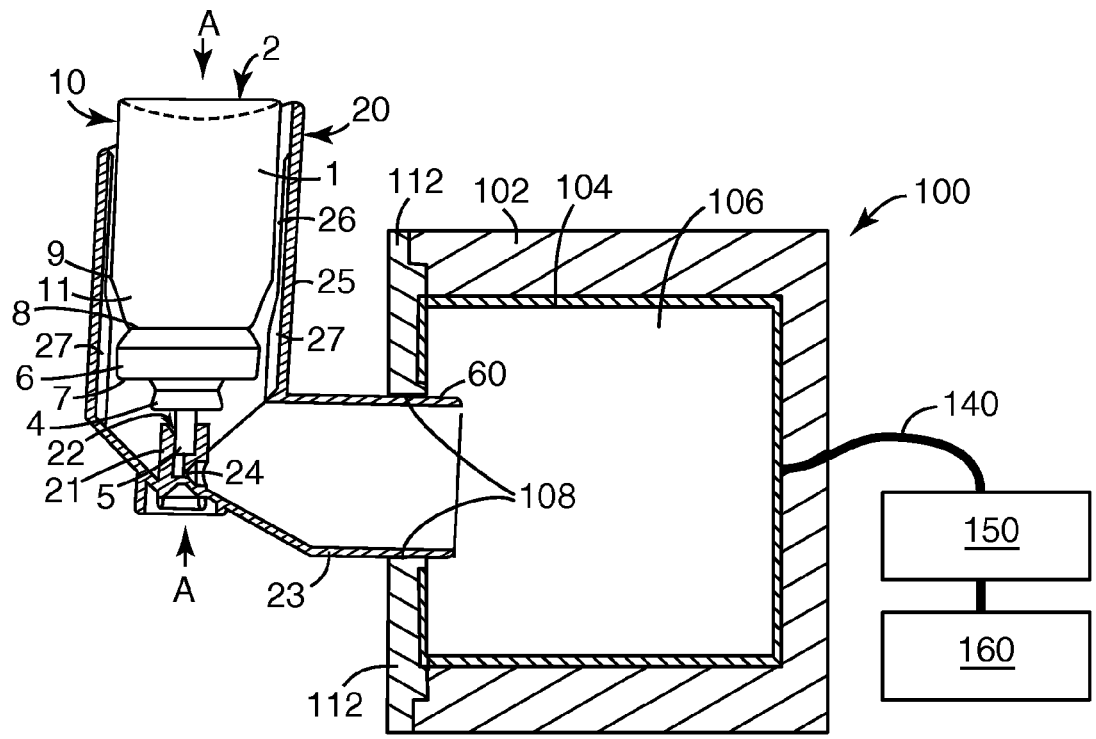
FIG. 3 is a side view of the inhaler of FIG. 1 inserted into the electrostatic charge measurement device of FIG. 2.

Use of the electrostatic measurement device 100 is shown in FIG. 3 where the mouthpiece 23 is inserted into the opening 110. The metered dose inhaler may be fired by moving the container 1 towards the support block 21 along the axis, marked as "A", thus allowing a metered dose of pressurized formulation to be expelled from the outlet member 5, thereby forming an aerosol that subsequently passes through the orifice 24 and the mouthpiece 23 and into the interior cavity 106 before depositing on the conductive lining 104. The electrostatic charge of the aerosol that deposits on the conductive lining 104 is measured (via wire 140 and electronics 150) and displayed on the meter 160.

As shown, the actuator is directly coupled to the detection portion (or detector) of the electrostatic measurement device and the emitted aerosol contacts the detector in the absence of an assisting airflow. That is, the pressurized canister provides sufficient energy to propel the emitted aerosol through the mouthpiece 23 to deposit on the lining 104. In such an arrangement, the electrostatic charge measurement will be representative of essentially the entire emitted aerosol. That is, the entire emitted aerosol will enter the Faraday cup and be measured, with the exception of relatively insignificant amounts of the aerosol which may deposit elsewhere, such as on the interior surfaces of the actuator, which may be able to escape through any slight openings where the actuator is placed within the adaptor, or which otherwise do not deposit in the Faraday cup.

In an alternative arrangement, one or more coupling members may be used to connect the mouthpiece 23 to the detector. For example, the mouthpiece 23 may be connected to an L-shaped member, such as a United States Pharmacopeia (USP) throat used for cascade impaction testing, such that part of the non-respirable fraction of the emitted aerosol deposits on the L-shaped member prior to entering the detector. In such an instance it may be desirable to pass an assisting airflow through the mouthpiece and coupling member to help carry the emitted aerosol into the detector. In another alternative arrangement, the coupling member may comprise a USP throat and one or more stages of a cascade impaction device. Such an arrangement may be used (in conjunction with an assisting airflow) to remove the non-respirable fraction of the emitted aerosol, thus delivering only the respirable fraction of the emitted aerosol to the electrostatic detector.

The electrostatic measurement device described above may be used to assess the suitability of a metered dose inhaler actuator by comparing the measured electrostatic charge to a predetermined specification range to make a determination whether the measured electrostatic charge is within or outside the predetermined specification range and accordingly whether the actuator is or is not acceptable. The actuator may be accepted if the electrostatic charge is within the predetermined specification range or rejected if the electrostatic charge is outside the predetermined specification range. An accepted actuator may be separated from the test canister after measuring the electrostatic charge and set aside for future use. For example, a product canister containing a medicinal aerosol formulation may be coupled to each actuator after separating the actuator from the test canister if the actuator is accepted in order to form a metered dose inhaler. The metered dose inhaler may subsequently be packaged for distribution to patients. A rejected actuator may be separated from the test canister after measuring the electrostatic charge and discarded.

Thus, in one aspect, each actuator in a production lot may be tested and accepted or rejected based on an individual measurement of electrostatic charge. A single test canister may typically contain enough pressurized formulation to provide up to about 240 actuations (i.e., emitted aerosol doses), sometimes between about 10 and about 240 and often can provide between about 30 and about 120 actuations. Thus a single test canister may be used to test up to about 240 actuators, or between about 30 and about 120 actuators by, in turn, coupling the test canister to a first actuator, firing the canister, measuring an electrostatic charge, accepting or rejecting the first actuator, and removing the test canister from the first actuator. A second (and subsequent) actuator(s) may then be coupled to the test canister and tested until the test canister is exhausted.

In another embodiment, a representative number of actuators are selected from a larger production lot of actuators and tested to determine if the larger production lot of actuators should be accepted or rejected. This may be done by any conventional statistical methodology, including for example, sampling procedures, such as Military Standard 105E, ANSI/ASQC Z1.4, Military Standard 414, and ANSI/ASQC Z1.9. For example, a fixed percentage of the actuators from a production lot of a given size may be tested and the production lot accepted if a predetermined percentage of the tested actuators are accepted. Alternatively, the average measured electrostatic charge of the aerosol emitted from the tested actuators may be compared to the predetermined specification range for electrostatic charge in order to accept or reject the production lot. The representative number of actuators tested will generally be selected so as to provide a desired confidence level (such as a 95% or 90% confidence level) for accepting or rejecting the production lot. Such a confidence level will generally depend on the estimated standard deviation of the electrostatic charge measurements, the representative number of actuators tested, and the number of actuators in the production lot.

It is generally advantageous to determine the acceptability of an actuator prior to its use in a finished product. A typical actuator is a relatively inexpensive, plastic molded part that is both easy to produce and has a low material cost. Conversely, a typical product canister is prepared in a relatively complicated manufacturing process and generally contains a number of different components (e.g., canister, valve, propellant, drug, excipients, etc.). As such, the finished product canister is a relatively expensive part. It is thus desirable to ensure that all actuators coupled to finished product canisters are acceptable, so as to reduce or eliminate the need to reject a finished product metered dose inhaler due to an out-of-specification actuator.

In one embodiment, each actuator is tested during the process of preparing a production lot of actuators so as to provide an in-process quality control mechanism. In this way, it can be determined if the actuator production process remains in control, or conversely the production process can be halted and examined if one or more actuators fails to meet the predetermined specification. In addition, it may be possible to detect minor variations in the electrostatic charge measurement associated with the tested actuators before the measured values deviate outside of the predetermined specification range, thus allowing adjustment of various processing parameters to ensure that the production process remains in control. This advantageously reduces, and ideally eliminates, waste of material and/or production time due to production of out-of-specification actuators.

The test canister is equipped with a valve and contains a pressurized propellant. Suitable propellants include fluorotrichloromethane, dichlorodifluoromethane, and 1,2-dichlorotetrafluoroethane. This invention finds particular use with aerosol formulations involving a propellant comprising 1,1,1,2-tetrafluoroethane (HFC-134a), 1,1,1,2,3,3,3-heptafluoropropane (HFC-227) or a mixture thereof. The test canister may contain a medicinal aerosol formulation comprising propellant, drug, and optional excipients.

As used herein, the term "drug," includes its equivalents, "bioactive agent," and "medicament" and is intended to have its broadest meaning as including substances intended for use in the diagnosis, cure, mitigation, treatment or prevention of disease, or to affect the structure or function of the body. The drugs can be neutral or ionic. Preferably, they are suitable for oral and/or nasal inhalation. Delivery to the respiratory tract and/or lung, in order to effect bronchodilation and to treat conditions such as asthma and chronic obstructive pulmonary disease, is preferably by oral inhalation. Alternatively, to treat conditions such as rhinitis or allergic rhinitis, delivery is preferably by nasal inhalation. Preferred drugs are asthma, allergy, or chronic obstructive pulmonary disease medications.

Suitable drugs include, for example, antiallergics, anticancer agents, antifungals, antineoplastic agents, analgesics, bronchodilators, antihistamines, antiviral agents, antitussives, anginal preparations, antibiotics, anti-inflammatories, immunomodulators, 5-lipoxygenase inhibitors, leukotriene antagonists, phospholipase $A_2$ inhibitors, phosphodiesterase IV inhibitors, peptides, proteins, steroids, and vaccine preparations. Exemplary drugs include adrenaline, albuterol, atropine, beclomethasone dipropionate, budesonide, butixocort propionate, ciclesonide, clemastine, cromolyn, epinephrine, ephedrine, fenoterol, fentanyl, flunisolide, fluticasone, formoterol, ipratropium bromide, isoproterenol, levalbuterol, lidocaine, mometasone, morphine, nedocromil, pentamidine isoethionate, pirbuterol, prednisolone, resiquimod, salmeterol, terbutaline, tetracycline, triamcinolone, and pharmaceutically acceptable salts and solvates thereof, and mixtures thereof. In one embodiment, the drug is a β2-adrenoreceptor agonist, such as albuterol, fenoterol, formoterol, isoproterenol, levalbuterol, pirbuterol, salmeterol, and pharmaceutically acceptable salts and solvates thereof, and mixtures thereof. A group of preferred drugs include albuterol, beclomethasone dipropionate, flunisolide, fluticasone, formoterol, ipratropium bromide, pirbuterol, salmeterol, and pharmaceutically acceptable salts and solvates thereof, and mixtures thereof.

The drug is present in the formulation in an amount sufficient to provide a predetermined number of therapeutically effective doses by inhalation, which can be easily determined by those skilled in the art considering the particular drug in the formulation. Optional excipients include cosolvents (e.g., ethanol, water), surfactants (e.g., oleic acid, sorbitan esters, polyoxyethylenes, glycols, oligolactic acids) and others known to those skilled in the art.

In one embodiment a product canister containing a medicinal aerosol formulation is coupled to each actuator after separating the actuator from the test canister if the actuator is accepted. The test canister may contain a medicinal aerosol formulation that is essentially the same as the product canister. That is, the test canister will contain the same ingredients at the same nominal amounts as the product canister, but it should be understood that it may not be identical due to ordinary variation in manufacturing processes. For example, a canister from a previous production lot of canisters for a particular product may be set aside for use in testing an actuator that is later coupled to a canister from a later production lot of canisters for the same product. In another embodiment, the test canister may contain a placebo aerosol formulation that is essentially the same as the medicinal aerosol formulation in the product canister with the exception that it lacks a drug. In still another embodiment, the test canister may contain any other test formulation which has been determined to be representative of an actual product canister insofar as its electrostatic charge properties when emitted from a metered dose inhaler. In still another embodiment, the test canister may comprise a pressurized aerosol formulation selected so as to provide a more sensitive electrostatic charge measurement response than that of the medicinal aerosol formulation in a product canister. For example, a pressurized aerosol formulation with a reduced amount of ethanol may allow for greater sensitivity in detecting variation between actuators, then a formulation with a higher amount of ethanol.

The measured electrostatic charge may be positive or negative and will depend on a number of parameters, including, but not limited to, the type of pressurized formulation in the canister, the type of canister and valve, the type of actuator, and the type of measurement device employed. The measured electrostatic charge is typically on the order of nanocoulombs or picocoulombs. In one embodiment, the measured electrostatic charge is positive and less than about 20 nanocoulombs and sometimes less than about 10 nanocoulombs. In another embodiment, the measured electrostatic charge is positive and less than about 200 picocoulombs and sometimes less than about 100 picocoulombs. In another embodiment, the measured electrostatic charge is negative and greater than about −20 nanocoulombs and sometimes greater than about −10 nanocoulombs. In another embodiment, the measured electrostatic charge is negative and greater than about −200 picocoulombs and sometimes greater than about −100 picocoulombs.

The predetermined specification range for determining if an actuator is acceptable or not may be selected as desired. In one embodiment, the predetermined specification range may be selected by statistical analysis of one or more production lots of tested actuators in order to determine the process capability. The process capability may be represented by the average (X) and standard deviation ($\sigma$) of the electrostatic charge measurements. A specification range may be selected, for example, by setting an upper limit of $(X+3*\sigma)$ and a lower limit of $(X-3*\sigma)$. In another embodiment, a correlation may be determined between the measured electrostatic charge and some other characteristic of the tested metered dose inhaler. For example, it is believed that an increase in the magnitude of electrostatic charge on an emitted aerosol may cause an increased attraction between the charged droplets or particles and surrounding surfaces, such as those found in the throat and respiratory tract of a patient. In some instances a correlation between measured electrostatic charge and the amount of emitted aerosol depositing in the throat section, or inlet port, (i.e., throat deposition) of an Anderson cascade impactor may be determined. A desired specification range may be known or selected for the amount of throat deposition (e.g., throat deposition specification is less than or equal to Y micrograms per actuation). A correlation between the electrostatic charge measurement and throat deposition is also determined (e.g., an electrostatic charge measurement of less than or equal to Z nanocoulombs per actuation corresponds to a throat deposition of less than or equal to Y micrograms per actuation). The specification range may then be set (e.g., electrostatic charge measurement specification is less than or equal to Z nanocoulombs per actuation).

In another embodiment, a group of actuators from a particular sub-lot of actuators may be tested for electrostatic charge and another group of actuators from the same sub-lot may be tested for another parameter, such as throat deposition. This can allow for determination of a correlation between measured electrostatic charge and some other property. A sub-lot is defined as consisting of actuators that would be expected to be nearly identical to each other. For example, a small group of actuators taken from a relatively short time period during manufacturing and/or prepared within a specific portion of the manufacturing apparatus, such as within a single cavity of a multi-cavity molding tool, could be defined as a sub-lot, since all of these actuators would be expected to be very similar.

In another embodiment, the present invention may further comprise a method of determining an electrostatic charge specification range. A test canister equipped with a valve and containing a pressurized propellant is provided. One or more actuators manufactured for use in a metered dose inhaler is provided. A first test is performed wherein each actuator is tested by coupling the canister to the actuator, positioning the actuator with respect to an electrostatic measurement device and firing the canister such that electrostatic charge from an aerosol emitted by the canister is measured by the electrostatic measurement device. A second test is performed wherein each actuator is tested by coupling the canister to the actuator, positioning the actuator with respect to a cascade impactor device, firing the canister, and measuring deposition of the medicinal aerosol formulation. A correlation between the measured electrostatic charge and the measured deposition of medicinal formulation is determined. An electrostatic charge specification range is then determined based on the correlation between measured electrostatic charge and the measured deposition of medicinal formulation. This specification range may then be used to determine if actuators are acceptable or not and whether they should subsequently be accepted and/or rejected as described above.

EXAMPLES

Electrostatic Charge Test Method

Electrostatic charge of metered dose inhalers (MDIs) was measured using an apparatus as described in FIGS. 2 and 3. A Monroe Electronics Nanocoulomb Meter Model 284 with a Faraday cup was used as the input source. The nanocoulomb meter is capable of direct measurement of charge in the range of one picocoulomb to two microcoulombs. The adaptor for the Faraday cup was fabricated to allow the MDI to be fired directly through the adaptor while containing the plume within the sensing electrode can of the faraday cup.

To obtain an electrostatic charge reading, an actuator is coupled with a test canister to prepare an MDI and inserted into the adaptor of the nanocoulomb meter. The adaptor may optionally be designed to allow for both electrostatic charge testing, and independently for Anderson Cascade Impactor testing. The nanocoulomb meter is zeroed before the MDI is fired. The MDI is fired and the reading from the nanocoulomb meter LCD display is recorded. The output from the nanocoulomb meter is the actual charge induced or deposited at the sensing electrode can of the Faraday cup in nanocoulombs (nC) and can be either positive or negative.

Unless otherwise noted, the reported electrostatic charge result is the average of three separate measurements taken for each test actuator. The meter was zeroed in between measurements, and a 15-second delay between firing the MDI was used to simulate the procedure used in Anderson Cascade Impactor testing.

Anderson Cascade Impactor Test Method

A standard airflow of 28.3 liters per minute was passed through the Anderson Cascade Impactor (ACI). Five shots were fired into the ACI, with a minimum of a 10 second delay taken between shots to allow the aerosol cloud to disperse. The impactor apparatus was then disassembled and the USP throat rinsed with methanol. The rinsate was analyzed by conventional high performance liquid chromatography (HPLC) methodology with a UV detector measuring at 238 nm in order to determine the total mass of beclomethasone dipropionate depositing on the throat per actuation. The HPLC mobile phase was 60% acetonitrile in ultra-pure water and a Supelcosil™ LC-18 column (150×4.6 mm, 5 μm particle size, Supelco, Bellefonte Pa.) was used.

Example 1

A correlation between USP inlet deposition, measured in an Anderson Cascade Impactor test, and measured electrostatic charge was determined as follows. An MDI was prepared by coupling a test canister to an actuator. The test canister was a 10 mL aluminum canister equipped with a 50 μL Spraymiser™ (available from 3M Co.) valve and contained a solution of beclomethasone dipropionate 0.084% (w/w) and ethanol 8.0% (w/w) in HFA-134a propellant. L-shaped, high density polyethylene actuators having a 0.3 mm diameter orifice, such as those used on QVAR™ (available from Ivax Co, Miami, Fla.) metered dose inhalers, were used.

The MDI was tested for USP inlet deposition according to the Anderson Cascade Impactor test. After testing, the canister was removed from the actuator and the actuator was dried. The actuator was again coupled to a test canister to prepare an MDI. Electrostatic charge was measured according to the test method above.

Figure 4:
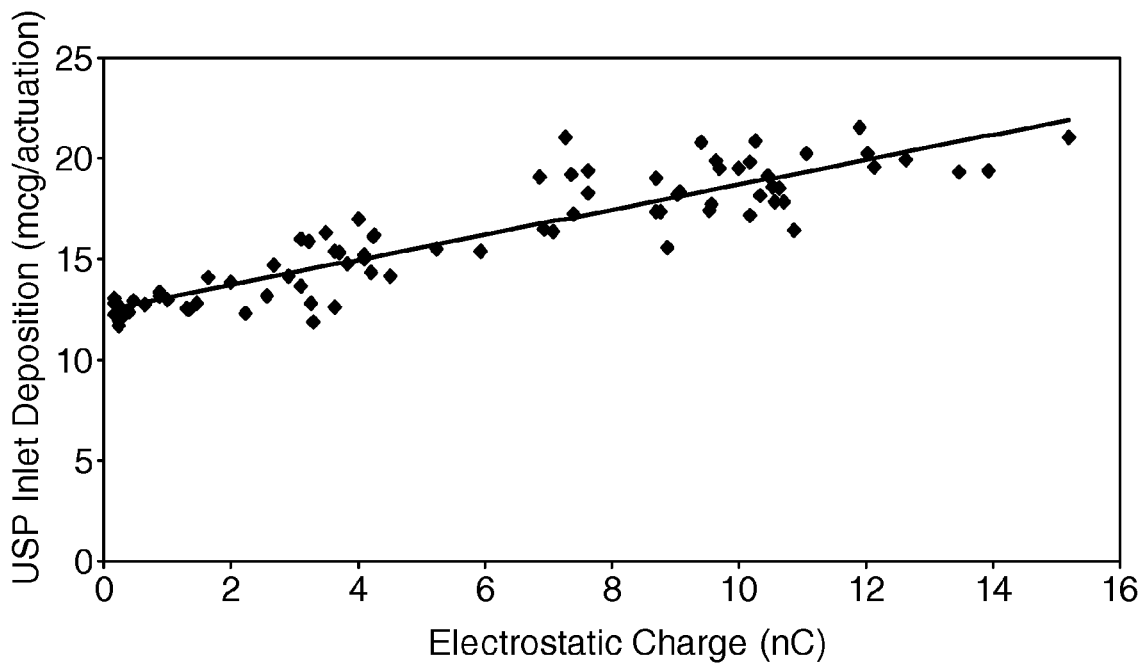
FIG. 4 is a plot of electrostatic charge vs. USP inlet deposition.

A plot of USP inlet deposition vs. measured electrostatic charge is shown in FIG. 4 along with a linear fit. Any suitable specification limit may be selected based on the correlation shown in FIG. 4. For example, the electrostatic charge could be given an upper specification limit of 8 nanocoulombs, which would correspond to an upper specification limit of USP inlet deposition of approximately 17 μg/actuation. Alternatively, an upper specification limit of 4 nanocoulombs could be chosen, corresponding to an upper specification limit of USP inlet deposition of approximately 15 μg/actuation.

Example 2

A correlation between USP inlet deposition, measured in an Anderson Cascade Impactor test, and measured electrostatic charge was determined as follows. A group of six or more actuators from a sub-lot of actuators were coupled to test canisters and tested for USP inlet deposition according to the Anderson Cascade Impactor test. The test canisters were 10 mL aluminum canisters equipped with a 50 μL Spraymiser™ valve and containing a solution of beclomethasone dipropionate 0.084% (w/w) and ethanol 8.0% (w/w) in HFA-134a propellant. L-shaped, high density polyethylene actuators having a 0.3 mm diameter orifice, such as those used on QVAR™ (available from Ivax Co, Miami, Fla.) metered dose inhalers, were used.

A group of five actuators from the same sub-lot of actuators were coupled to test canisters and the measured electrostatic charge was determined. A sub-lot was defined as consisting of actuators that would be expected to be nearly identical to each other. For example, a small group of actuators taken from a relatively short time period during manufacturing and prepared within a specific portion of the manufacturing apparatus, such as within a single cavity of a multi-cavity molding tool, could be defined as a sub-lot.

Figure 5:
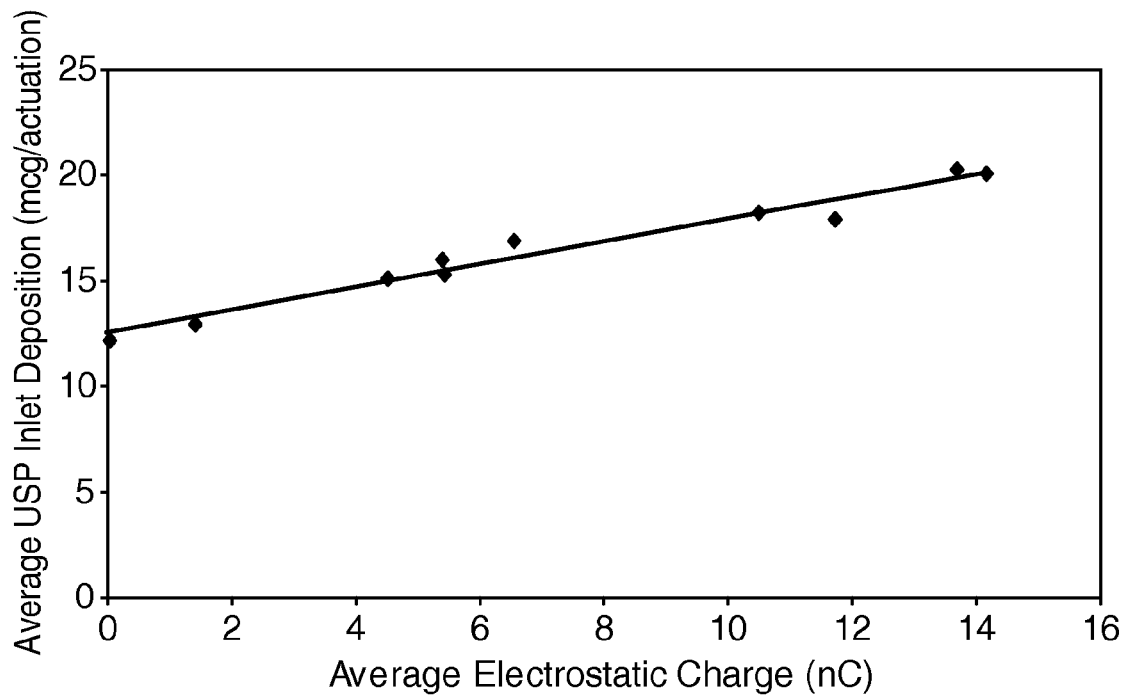
FIG. 5 is a plot of electrostatic charge vs. USP inlet deposition.

A plot of USP inlet deposition vs. measured electrostatic charge is shown in FIG. 5 along with a linear fit. Any suitable specification limit may be selected based on the correlation shown in FIG. 5. For example, the electrostatic charge could be given an upper specification limit of 10 nanocoulombs, which would correspond to an upper specification limit of USP inlet deposition of approximately 18 μg/actuation. Alternatively, an upper specification limit of 4 nanocoulombs could be chosen, corresponding to an upper specification limit of USP inlet deposition of approximately 15 μg/actuation.

Example 3

Figure 6:
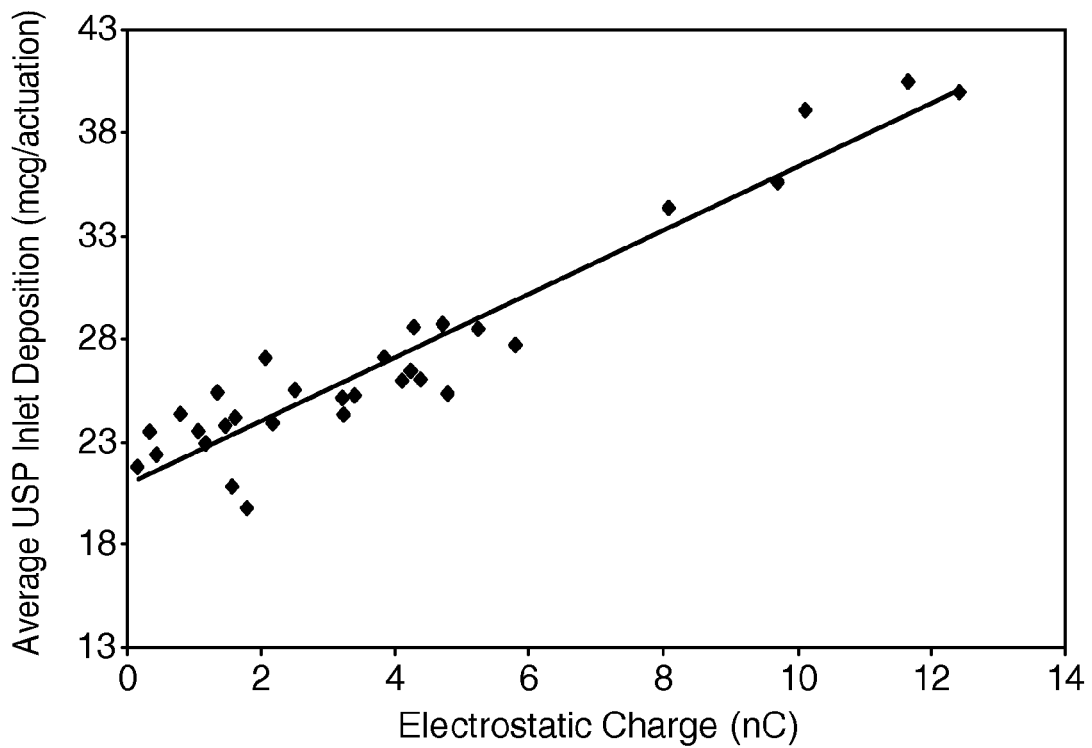
FIG. 6 is a plot of electrostatic charge vs. USP inlet deposition.

A correlation between USP inlet deposition and measured electrostatic charge was determined according to the general procedure in Example 2, with the exception that the test canisters comprised 0.167% (w/w) beclomethasone. A plot of USP inlet deposition vs. measured electrostatic charge is shown in FIG. 6 along with a linear fit. Any suitable specification limit may be selected based on the correlation shown in FIG. 6.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A method of assessing the suitability of a metered dose inhaler actuator comprising the steps of:
    a) providing a test canister equipped with a valve and containing a pressurized propellant;
    b) providing one or more actuators manufactured for use in a metered dose inhaler;

c) testing the one or more actuators, wherein each actuator is tested by coupling the canister to the actuator, positioning the actuator with respect to an electrostatic measurement device and firing the canister such that electrostatic charge from an aerosol emitted by the canister is measured by the electrostatic measurement device;

d) comparing the measured electrostatic charge to a predetermined specification range to make a determination whether the measured electrostatic charge is within or outside the predetermined specification range and accordingly whether the actuator is or is not acceptable.

2. A method as claimed in claim 1 wherein the actuator is separated from the test canister after measuring the electrostatic charge.

3. A method as claimed in claim 2 wherein a product canister containing a medicinal aerosol formulation comprising a drug is coupled to each actuator determined to be acceptable after separating the actuator from the test canister to prepare a metered dose inhaler.

4. A method as claimed in claim 1 wherein the propellant is selected from 1,1,1,2-tetrafluoroethane (HFC-134a), 1,1,1,2,3,3,3-heptafluoropropane (HFC-227) or a mixture thereof.

5. A method as claimed in claim 3 wherein the test canister contains a medicinal aerosol formulation that is essentially the same as the medicinal aerosol formulation in the product canister.

6. A method as claimed in claim 3 wherein the test canister contains a placebo aerosol formulation that is essentially the same as the medicinal aerosol formulation in the product canister with the exception that it lacks a drug.

7. A method as claimed in claim 1 wherein each actuator that is determined to be non-acceptable is rejected and discarded.

8. A method as claimed in claim 1 wherein the provided actuator is directly coupled to the detection portion of the electrostatic measurement device and the emitted aerosol contacts the detection portion of the electrostatic measurement device in the absence of an assisting airflow.

9. A method as claimed in claim 1 wherein the electrostatic charge of essentially the entire emitted aerosol is measured.

10. A method as claimed in claim 1 wherein each actuator in a production lot is tested and accepted or rejected based on an individual measurement of electrostatic charge.

11. A method as claimed in claim 1 wherein each actuator is tested during the process of preparing a production lot of actuators so as to provide an in-process quality control mechanism.

12. A method as claimed in claims 1 wherein a representative number of actuators are selected from a larger production lot of actuators and tested to determine if the larger production lot of actuators should be accepted or rejected.

13. A method as claimed in claim 1 wherein the predetermined specification range is less than or equal to 10 nanocoulombs.

14. A method as claimed in claim 1 wherein 10 to 240 actuators are tested with a single test canister.

15. A method as claimed in claim 1 and further comprising the steps of:

e) providing a test canister equipped with a valve and containing a pressurized medicinal aerosol formulation;

f) providing one or more actuators manufactured for use in a metered dose inhaler;

g) performing a first test of the one or more actuators, wherein each actuator is tested by coupling the canister to the actuator, positioning the actuator with respect to an electrostatic measurement device and firing the canister such that electrostatic charge from an aerosol emitted by the canister is measured by the electrostatic measurement device;

h) performing a second test of the one or more actuators, wherein each actuator is tested by coupling the canister to the actuator, positioning the actuator with respect to a cascade impactor device, firing the canister, and measuring deposition of the medicinal aerosol formulation;

i) determining a correlation between the measured electrostatic charge and the measured deposition of medicinal formulation; and j) determining an electrostatic charge specification range based on the correlation between measured electrostatic charge and the measured deposition of medicinal formulation, wherein steps e) to j) are performed prior to performing steps a) to d) and the predetermined specification range of step d) corresponds to the electrostatic charge specification range determined in step j).

16. A method as claimed in claim 15 wherein the test canister provided in step a) comprises a placebo aerosol formulation.

17. A method as claimed in claim 3 wherein the test canister comprises a pressurized aerosol formulation selected so as to provide a more sensitive electrostatic charge measurement response then that of the medicinal aerosol formulation in the product canister.

* * * * *